United States Patent [19]

Khwaja

[11] Patent Number: 5,565,200
[45] Date of Patent: *Oct. 15, 1996

[54] PHARMACEUTICAL PREPARATIONS DERIVED FROM KOREAN MISTLETOE

[75] Inventor: Tasneem A. Khwaja, Newport Beach, Calif.

[73] Assignee: University of Southern California, Los Angeles, Calif.

[ * ] Notice: The term of this patent shall not extend beyond the expiration date of Pat. No. 5,547,674

[21] Appl. No.: 422,438

[22] Filed: Apr. 14, 1995

[51] Int. Cl.$^6$ ................................................. A61K 35/78
[52] U.S. Cl. ............................... 424/195.1; 514/2; 514/8; 514/885; 514/934
[58] Field of Search ........................... 424/195.1; 514/2, 514/8, 885, 934

[56] References Cited

U.S. PATENT DOCUMENTS

| | | | |
|---|---|---|---|
| 3,394,120 | 6/1968 | Vester | 530/379 |
| 3,472,831 | 10/1969 | Vester | 530/379 |
| 3,475,402 | 10/1969 | Vester | 530/379 |
| 4,525,344 | 6/1985 | Tutsky | 424/73 |
| 4,590,071 | 5/1986 | Scannon et al. | 424/85 |
| 4,784,849 | 11/1988 | Tutsky | 424/73 |
| 4,861,581 | 8/1989 | Epstein et al. | 604/1.1 |
| 4,894,443 | 1/1990 | Greenfield et al. | 530/388 |
| 4,966,577 | 10/1990 | Crosson et al. | 604/20 |
| 5,019,368 | 5/1991 | Epstein et al. | 424/1.1 |
| 5,093,475 | 3/1992 | Carroll et al. | 530/391.9 |
| 5,183,904 | 2/1993 | Carroll et al. | 549/68 |

OTHER PUBLICATIONS

S. Krager AG, "Cancer of the Exocrine Pancreas," *Oncology*, vol. 12, pp. 1–70, 1986.
Gabius et al., "Cytokines as Mediators in Rationally Standardized Mistletoe Therapy," *Abstracts of the Third International Conference of Anticancer Research*, 16–20 Oct. 1990, Marathon, Greece, No. 385, pp. 1473–1474.
Rentea et al., "Biologic Properties of Iscador: A *Viscum album* Preparation," *Laboratory Investigation*, vo. 44, No. 1, pp. 43–48, 1981.
Ribéreau-Gayon et al., "Effects of mistletoe (*Viscum album* L.) extracts on cultured tumor cells," *Experientia* 42, pp. 594–599 (1986).
Gabius et al., "The immunomodulatory β–Galactoside–Specific Lectin from Mistletoe: Partial Sequence Analysis, Cell and Tissue Binding, and Impact on Intracellular Biosignalling of Monocytic Leukemia Cells," *Anticancer Research* 12:669–676 (1992).
Kayser et al., "Analysis of tumour necrosis factor α–specific, lactose–specific and mistletoe lectinspecific binding sites in human lung carcinomas by labelled ligands," *Virchows Archiv A Pathol Anat* (1992) 421:345–349.

Gabius et al., "The galactoside–specific lectin from mistletoe as biological response modifier," *Int'l Journal of Oncology*, 1, 705–708, 1992.
Hajto, "Modulatory Potency of the β–Galactoside–specific Lectin from Mistletoe Extract (Iscador) on the Host Defense System in Vivo in Rabbits and Patients," *Cancer Research*, 49, 4803–4808, 1991.
Beuth et al., "Behavior of lymphocyte subsets and expression of activation markers in response to immunotherapy with galactoside–specific lectin from mistletoe in breast cancer patients," *Clin. Investig.* (1992) 70:658–661.
Bloksma, "Stimulation of Humoral and Cellular Immunity by Viscum Preparations," pp. 2–8.
Khwaja et al., "Experimental Basis for the Use of 'Iscador' in Cancer Treatment," *13th International Congress of Chemotherapy*, Vienna 28th Aug. to 2nd Sep. 1983.
Khwaja et al., "Isolation of biologically active alkaloids from Korean mistletoe *Viscum album, coloratum*," Experientia 36 (1980).
Khwaja et al., "Studies on Cytotoxic and Immunologic Effects of *Viscum Album* (Mistletoe)," *AACR* 22, 253, 1981.
Khwaja et al., "Isolation of Cytotoxic Proteins from *Viscum Album, coloratum*," *AACR Abstract Form*, 1985.
Khwaja et al., "Isolation of Cytotoxic Lectin from *Viscum Album, Coloratum*," *Proceedings of AACR*, vol. 28, Mar. 1987, p. 303.
Khwaja et al., "Characterization of Biologically Active Components of *Viscum Album* (Mistletoe)," Poster Abstract Form for publication in the *Journal of Cancer Research Clinical Oncology*, 1989.
Khwaja et al., "Characterization of cytotoxic lectins isolated from *Viscum album, Coloratum*," *AACR*, vol. 30, p. 576, 1989.
Khwaja et al., "Characterization of biologically active components of Mistletoe," *AACR*, 1990.
Khwaja et al., "Biopharmacological Studies of Different Components of *Viscum album* (Mistletoe)," *Abstracts of the Third International Conference of Anticancer Research*, pp. 1374–1375, 1990.

*Primary Examiner*—John W. Rollins
*Attorney, Agent, or Firm*—Poms, Smith, Lande & Rose

[57] ABSTRACT

An aqueous mistletoe extract made from Korean mistletoe. The extract is useful in treating AIDS, cancers and other diseases where the immune system is suppressed. The extract is a pharmaceutical grade extract which has specific levels of lectins, viscotoxins and alkaloidal compounds which combine to provide the observed pharmacological activity. A lectin fingerprint of the extract is also provided.

12 Claims, 1 Drawing Sheet

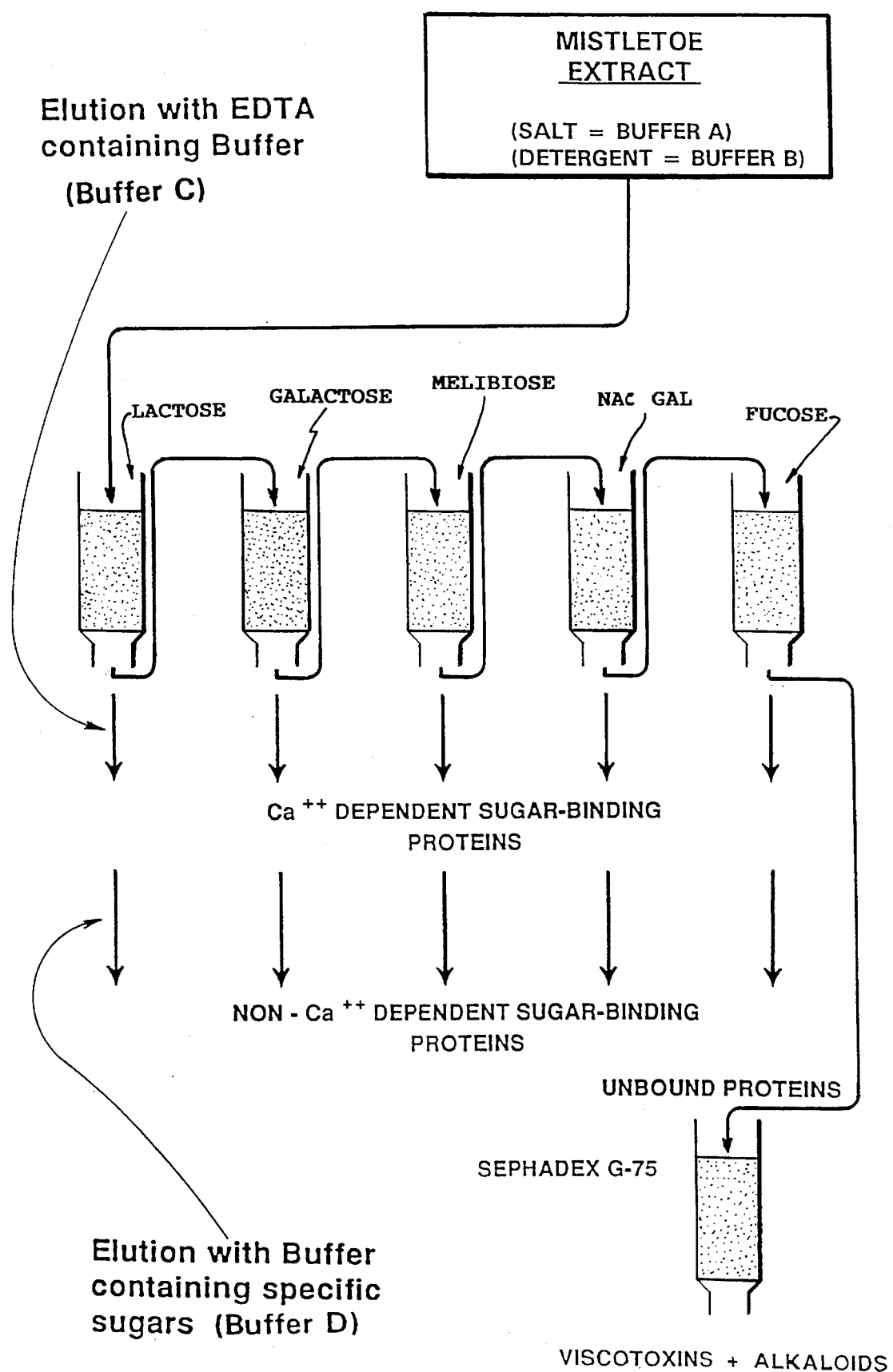

PHARMACEUTICAL PREPARATIONS DERIVED FROM KOREAN MISTLETOE

BACKGROUND OF THE INVENTION

1. Field of the Invention

The present invention relates generally to the treatment of Acquired Immune Deficiency Syndrome (AIDS) and other diseases or conditions where an individual's immune system is suppressed. More particularly, the present invention relates to pharmaceutical preparations which are useful in treating AIDS and other immune system disorders where the preparations include active ingredients that are derived from mistletoe.

2. Description of the Related Art

AIDS is associated with a highly infectious retrovirus called Human Immunodeficiency Virus (HIV). This virus multiplies in human lymphocytes and macrophages and with the help of a viral reverse transcriptase in incorporated into the cellular genome (as pro-viral DNA). In the acute infectious stage, the virus kills most of the infected lymphocytes, especially T4 lymphocytes. T4 lymphocytes play a central role in host immune response. T4 cells, on stimulus from a foreign antigen in presence of interleukin-1 (IL-1), undergo a series of biochemical changes which activate expression of a number of genes including those for interleukin-2 (IL-2), IL-2 receptors and gamma interferon. Substances secreted by 'activated' T4 cells stimulate maturation of B cells (plasma cells) which secrete antibodies (humoral immune response) and help in maturation of (cytotoxic) T8 cells which eliminate (pathogen) infected cells, including cancer (cellular immune response). T4 cells also suppress activation of T8 cells once the infection is under control. IL-2 secreted by T4 cells binds with IL-2 receptors to stimulate division of these cells to approximately 1000 memory clones with antigen specific memory. Thus, T4 cells play a central role in host immune response.

T4 cells infected with HIV carry pro-viral DNA in their genome. Stimulation of infected T4 cells results in expression of its genes including those for HIV. The synthesis of viral RNA and proteins in the infected cells results in production of virus particles. The virus particles, as they burst out of the infected T4 cells, also destroy the host lymphocytes and restrict the production of memory clones. This depletion of T4 cells in HIV infected patients leaves them without the ability to fight even minimal infections. Thus, AIDS patients contract terminal opportunistic diseases like pneumonia, caused by a generally harmless protozoan, *Pneumocystis carinii*, or a cancer called Kaposi's sarcoma, a tumor of blood vessel tissue, in skin or internal organs.

Numerous treatment protocols have been developed for treating AIDS. Immunotherapy is one form of treatment which has been investigated extensively. The two exemplary types of immunotherapy used for treating AIDS are: (a) monoclonal antibodies and (b) intravenous immunoglobulin (IVIG). Monoclonal antibodies are generally murine proteins that must be "humanized" with genetic engineering to minimize the human anti-murine antibody (HAMA) response. An advantage of IVIG over monoclonal antibodies is that the HAMA response is minimal since IVIG are human proteins. In addition, IVIG is readily available from blood bank plasma. However, IVIG has usually been administered only after a patient develops AIDS in an attempt to limit infection by opportunistic viruses other than HIV.

IVIG is FDA-approved and is presently commercially available for treatment of viral and other diseases in either intravenous or intramuscular formulations. Different forms of IVIG can be generated by screening blood bank plasma for donors that have a particularly high titer of antibody directed against a specific virus. Therefore, pooling the plasma from these viral-exposed donors provides a form of IVIG that contains high titers of antibodies targeting a specific virus, such as HIV. The use of HIV sero-positive plasma in the generation of HIV immune globulin (HIVIG) has been described and is presently in clinical trials for the treatment of AIDS. Similarly, other forms of viral specific human immune globulin are presently being studied for the treatment of other viral diseases.

The above forms of immunotherapy (e.g., monoclonal antibodies, IVIG, HIVIG) for the treatment of AIDS is limited by the poor cellular uptake of the monoclonal antibody or immune globulin. This is because the virus replicates in the intracellular space of cells; therefore, effective neutralization of the virus requires "intracellular immunization." Owing to the poor transport of monoclonal antibodies or immune globulins into cells, these agents generally allow only for intravascular or extracellular immunization in vivo in living subjects. For example, neutralizing monoclonal antibodies or HIVIG which prevent the replication of HIV in either mouse or chimpanzee models have been shown to be effective only when the immunotherapeutic is administered immediately prior to viral infection. Treatment with IVIG or HIVIG prior to infection gives the circulating antibodies the opportunity to neutralize the virus as it enters the bloodstream. However, this immunotherapeutic is not effective in pre-existing disease because the immunotherapeutic does not gain access to the intracellular space where the virus replicates.

Another approach has involved the development of a variety of vaccines which have been proposed for use in immunizing individuals against the AIDS virus either before or during the early stages of infection. One such proposed vaccine is an AIDS viral decoy which is described in U.S. Pat. No. 5,334,394. The viral decoy is composed of nanocrystalline particles which mimic the viral core of the AIDS virus. The inert cores are coated with antigenic AIDS viral fragments to produce a non-infective agent which shows promise as an effective immunization agent.

Still other approaches have involved treatments using a wide variety of pharmaceutical agents, such as azidothymidine (AZT), 2',3'-dideoxyinosine (ddI) and 2',3'-dideoxycytidine (ddC). These nucleoside analogs inhibit reverse transcriptase, the enzyme which converts viral RNA to proviral DNA, but do not prevent expression of viral genome and onset of the latent disease. AZT has been shown to prolong the life of AIDS patients for at least one year. However, use of these drugs is limited due to serious toxic side effects including immunosuppression.

Another class of anti-AIDS drugs are protease inhibitors. These drugs prevent the replication of AIDS virus by interfering with the production of proteins vital for the assembly of virus particles. Individually, these products have not been effective due to emergence of resistance to these treatments. A combination of these treatments has been proposed to increase efficacy of these drugs.

Purified IL-2 which stimulates the production of CD4 cells has been reported to improve CD4 count of AIDS patients. The drug is very expensive and causes serious side effects which have symptoms similar to acute influenza. The toxicity of IL-2 may be due to an excess of the growth factor in the cellular system which could overwhelm the feedback control systems, which maintain the integrity and control of the host immune response.

The wide variety of AIDS treatment protocols which are presently available provide an equally wide array of treatment efficacies. To date, none of the procedures have been found to be entirely satisfactory when taken alone or in combination. Accordingly, there is a continuing and pressing need to develop new pharmaceutical preparations and treatment protocols which are useful in treating individuals infected with the AIDS virus.

Plants have proved to be a rich source of drugs for modern medicine. There are hundreds of plants and herbs which have been used for the treatment of different diseases all over the world. Most of these treatments are non-toxic and non-immunosuppressive. There are quite a number of modern chemotherapeutic drugs, like Vinca alkaloids, adriamycin and taxol, which have been isolated from natural sources and are currently used to treat different malignancies. The major disadvantage in use of purified single components is emergence of drug resistance and serious toxic side effects at therapeutic doses. Combination therapies, as evidenced by herbal products, reduce the emergence of drug resistances.

Mistletoe plants belong to the genus Viscum (family, Loranthaceae), which contains a variety of semiparasitic plants found all over the world. The European variety of mistletoe is called *Viscum album lanatum* which grows on deciduous trees like apple, oak, pine, and sycamore. The plant in ancient Europe was held in great reverence and respected by Druids, as it was used by pagan priests to effect "wonderful" cures. This may be the reason that it has been incorporated as a part of home decoration at Christmas. The medicinal properties of mistletoe include many domestic remedies, e.g., as a tonic in nervous disorders, for treatment of convulsions, delirium, and epilepsy.

Aqueous extracts of mistletoe have been made commercially available in Europe under the tradenames "Iscador," "Helixor" and "Plenosal." The better known "Iscador" is available in the form of different preparations for the treatment of postoperative human neoplasm, and there are several reports of its beneficial effects for breast, lung, and colon carcinoma. However, due to the lack of carefully controlled clinical studies, the merits of Iscador use for cancer treatment have been controversial. The major problems involved in the use of mistletoe preparations, like most herbal products, have been the lack of methods for the manufacture of a standard preparation and uniform quality control. These preparations, especially Iscador, unlike conventional cancer treatments, are nontoxic and effectively induce a beneficial immune stimulatory response in cancer patients.

SUMMARY OF THE INVENTION

In accordance with the present invention, it was discovered that a pharmaceutical preparation composed of certain amounts of specific lectins, viscotoxins and alkaloids is especially effective in treating patients infected with the AIDS virus. The pharmaceutical preparation is derived from mistletoe belonging to the species *Viscum album coloratum* which is found in South Korea growing on oak trees.

The pharmaceutical preparation in accordance with the present invention is an extract of Korean mistletoe which has the following lectin, viscotoxin and alkaloid composition which is expressed as µg per ml of 1 percent extract:

total lectins=3.0–6.0 µg/ml extract viscotoxins=10–40 µg/ml extract alkaloids=10–50 µg/ml extract As a feature of the present invention, the Korean mistletoe-derived pharmaceutical preparation is used alone or in combination with other therapies to provide an effective treatment for AIDS and other conditions involving suppressed immune systems. The combined ingredients in the preparation have been found to be more effective when used together in the preparation than when the ingredients are administered alone. The preparation is an aqueous based solution which is injected subcutaneously or intravenously into the patient in accordance with conventional AIDS treatment protocols.

The above described and many other attendant features and advantages of the present invention will become better understood by reference to the following detailed description of the invention when taken in conjunction with the accompanying FIGURE.

BRIEF DESCRIPTION OF THE DRAWINGS

The FIGURE is schematic representation of an exemplary procedure for isolating specific active ingredients from mistletoe extracts which are used in formulating the pharmaceutical preparation in accordance with the present invention. The procedure is also used to verify that a given pharmaceutical preparation meets the compositional requirements of the present invention.

DETAILED DESCRIPTION OF THE INVENTION

The pharmaceutical preparation in accordance with the present invention is derived from *Viscum album coloratum* which is a mistletoe species that is found in South Korea growing on oak trees. The preparation may be prepared from other mistletoes provided that the final preparation ingredients and concentrations are adjusted to meet the formulation requirements set forth below.

Mistletoe is a parasite which grows on a variety of deciduous trees including apple, cherry, oak, ash hawthorn, lime and acorn. Since 1980, the investigation of mistletoe has increased due to its immunomodulatory properties and potential usefulness in treating cancer. See International Journal of Cancer Research Treatment—ONCOLOGY—Vol. 43, Supplement 1, 1986. A major problem facing mistletoe investigators involves the analysis, identification and standardization of the pharmacologically active ingredients in mistletoe and extracts thereof. This problem is exacerbated by the fact that the numerous complex ingredients which are found in mistletoe extracts vary widely in type and amount depending upon the species of mistletoe, the location where the plant is grown, the time of year when the plant is harvested, the particular host tree, the extraction procedure used and a number of other factors.

The principal classes of ingredients in mistletoe which have been found to provide pharmacological activity include lectins, viscotoxins and alkaloids. The viscotoxins include a number of low molecular weight proteins. These proteins are toxic and their mechanism of action is believed to be due to inhibition of DNA synthesis. As single components, the viscotoxins lack therapeutic activity. The lectins are high molecular weight glycoproteins which show specific binding characteristics to terminal carbohydrate molecules of cell surface proteins. The lectins consist of two arms. The toxic arm (chain A) has been shown to inhibit ribosomal protein synthesis. The B chain exhibits sugar specific cell surface binding characteristics. These binding properties to macrophages or T-lymphocytes are believed to be responsible for mistletoe extract in T4 cell activation resulting in effective stimulation of host immune response.

The alkaloids contained in the alkaloidal fraction are nitrogenous compounds which include small chains of polysaccharides which are tightly bound (may be covalently) to mistletoe proteins, including lectins. The alkaloids are extracted and separated by chloroform and give a positive test with Dragendorff reagent. Individually these molecules exhibit anticancer activity in vitro and modest effects in vivo. It is believed that alkaloids play a central role in modulating the therapeutic effects of lectins. Removal of alkaloids increases the toxicity of lectins and effects their therapeutic index. The presence of alkaloids is believed to be essential for therapeutic activities of mistletoe based therapeutics. Viscotoxins are also believed to be required to increase therapeutic activity of lectins. Accordingly, the present invention requires that all three ingredients, i.e. lectins, viscotoxins and alkaloids be present in the amounts set forth below.

Although the types of pharmacologically important compounds which are generally present in mistletoe have been identified, investigators have not had a great deal of success with respect to standardizing the multitude of available extracts to establish if one or more ingredients are responsible for the observed bioactivity and whether the ingredients act together or may be effective individually. The extremely diverse nature of mistletoe extracts and the inherent variability in extract compositions makes it imperative that the initial extract be analyzed to establish whether the active ingredients required in accordance with the present invention are present and that the relative amounts of the active ingredients fall within the required ranges.

The pharmaceutical preparations in accordance with the present invention are aqueous extracts of Korean mistletoe which contain about 3.0 to 6.0 µg of lectins, 10–40 µg of viscotoxins and 10–50 µg of alkaloids per ml of 1 percent extract. A 1 percent extract is defined for the purposes of this specification as being one where the relative amount of plant weight extracted to aqueous extract corresponds to 1 gram of mistletoe plant material per 100 ml of aqueous extractant. For a 10 percent extract, the 1 percent extract levels set forth above will be 10 times greater. Preferably, the pharmaceutical preparation will contain about 4.0 to 5.0 µg of lectins, 20–30 µg viscotoxins and 14–25 µg of alkaloids. Even more, preferably the pharmaceutical preparation will contain about 4.9 µg g lectins; about 72 µg unbound proteins which contain from 10–40 µg of viscotoxins; and about 14 µg alkaloids per 1 ml of 1 percent extract.

The pharmaceutical preparation can be prepared by combining the active ingredients which have been extracted and isolated from a wide variety of different mistletoe species. However, the extracts of many species may not produce all or even some of the specific lectins, viscotoxins or alkaloids required for the preparation and it is unlikely that the extracts will contain the required relative amounts of ingredients. Accordingly, one would be required to prepare numerous different extracts, separate them into their individual lectin, alkaloid and viscotoxin components and then recombine the ingredients to produce pharmaceutical preparations in accordance with the present invention. This is a time consuming and tedious process which can be used to prepare the preparations, but it is not recommended.

The preferred process for making the pharmaceutical preparation is to prepare an aqueous extract of *Viscum album coloratum* which contains the required levels of active ingredients. Aqueous extracts from this particular species of mistletoe have been found to contain active ingredient profiles which conform closely with the compositional requirements of the pharmaceutical preparation in accordance with the present invention. However, the level and types of lectins, viscotoxins and alkaloids will vary even among the mistletoe which belong to the this preferred species. Variations in compositional make-up are caused by a number of different factors including host plant, time of harvesting and location. In order to limit the amount of ingredient adjustments which must be made, it is preferred that the *Viscum album coloratum* be harvested from oak trees during the months of December, January and February and that the oak trees be located in South Korea. It has been found that aqueous extracts from this particular type of mistletoe contain suitable amounts of the active ingredients which meet the requirements of the present invention with little or no adjustment in concentration levels or addition of missing ingredients.

An exemplary procedure for preparing a pharmaceutical grade extract in accordance with the present invention is as follows:

Mistletoe powder is initially prepared using any of the known powdering procedures. The mistletoe powder is preferably prepared from the *Viscum album, coloratum* species which is found on oak trees in and around Seoul, South Korea. It is preferred that the mistletoe be flash frozen shortly after harvesting and then ground to a powder in the frozen state. Flash freezing with liquid nitrogen or similar cryogenic liquid is preferred. The entire mistletoe plant may be used in preparing the powder. The preferred harvesting time is when the berries are ripe (December–February).

The mistletoe powder is extracted using a substantially pure aqueous solution. The extracting solution may include additional ingredients to enhance the extraction process. The extract may include a salt such as calcium chloride or sodium chloride in an amount sufficient to enhance extraction of proteins from the mistletoe sap. Salt concentrations on the order of 0.02M are preferred. Detergents such as TRITON® x-100 may also be added to enhance extraction of protein from the plant cell walls. The extractant is preferably buffered with Tris to a pH of about 7.8. The extraction procedure should utilize an amount of extractant relative to the amount of mistletoe being extracted which will produce levels of proteins as set forth below. Preferably, between about 100 and 400 grams of mistletoe powder will be extracted with between about 1000 and 4000 ml of aqueous solution (10 percent extract). The powder is mixed in the solution and left to stand for from one to two hours. The powder particulates remaining after the extraction period are separated by filtration or other conventional separation technique to produce the aqueous mistletoe extract. Due to the variable and relatively unknown nature of all of the complex ingredients in mistletoe, it is preferred that all of the above listed preferred steps be followed in order to optimize the number of extract preparations which meet the requirements of the method of the present invention.

After the extraction procedure has been completed, any detergent or other pharmaceutically unacceptable compound present in the extract is removed using conventional separation techniques. The remaining extract is then ready for formulation into the pharmaceutical preparation. The straight extract may meet the compositional requirements of the present invention. However, it may also require minor adjustments to ingredient levels which may be accomplished by a general dilution or dehydration of the extract and/or the addition of specific ingredients. Whether or not adjustments need to be made is determined by quantitatively analyzing the extract to establish the levels of each ingredient present in the extract. An exemplary analysis procedure is as follows:

One method for analyzing the lectin (sugar-binding protein) content, alkaloidal fraction and viscotoxin levels in the extract involves the use of ammonium sulfate precipitation. In this method, the total proteins of mistletoe preparation is precipitated with 70% ammonium sulfate. The preparation is centrifuged to provide a precipitate which contains a mixture of the viscotoxins and the sugar-binding promins (lectins). This mixture is separated on a acid-hydrolysed Sepharose 4B column with the two separate viscotoxin and lectin fractions being quantitated according to conventional protein quantitative analysis such as Biorad assay.

The ammonium sulfate-supernatant, which contains the alkaloidal fraction, is lyophilized and the alkaloids are extracted with chloroform. The chloroform residue provides the total alkaloids which are quantitated by weighing the dried extract which gives characteristic color reaction with Dragendorff reagent.

In a preferred embodiment of the present invention, a portion of the mistletoe extract is further analyzed to determine the concentration of individual lectins (sugar-binding proteins) in the extract. The analysis is preferably conducted by affinity column chromatography as schematically represented in the FIGURE. The analysis is preferably conducted in two stages in order to separate the proteins which require $Ca^{++}$ for binding to sugar and those proteins which are non-$Ca^{++}$ dependent. A Buffer which contains ethylene diamine tetraacetic acid (EDTA) or other chelating agent is used to elute the $Ca^{++}$ dependent sugar-binding proteins from affinity columns which have been treated with the specific sugars of interest, i.e. lactose, galactose, melibiose, N-acetyl-N-galactosamine and fucose. The resulting fractions are then analyzed for protein content. Other affinity columns based on similar principles of chromatography may also be used, e.g. mannose, rhamnose, maltose, asialofeutin, glucosamine and n-acetyl glucosamine. The appropriate levels and activities of the lectins in the extract which are specific for these sugars can be established by measuring their levels in extracts which meet the criteria for sugar-specific lectins set forth above.

After elution of each of the sugar-specific affinity columns with EDTA-containing buffer, the columns are then eluted with buffers that each contain the sugar which corresponds to the sugar bound to the respective affinity columns. Sepharose® 4B is a preferred column material. The various fractions resulting from this second elution contain the non-$Ca^{++}$ dependent sugar-binding proteins. The protein content of each of these fractions is also quantitatively determined. Protein quantitation can be performed using any of the conventional quantitative analytical procedures including ninhydrin based tests, spectroscopic determination and Bio-Rad or Pierce analysis. The use of multiple buffers as described above is preferred so that the total level of each type of protein is determined. Affinity column chromatography is preferred because it is a conventional separation technique which is well-known to those of ordinary skill in the art and which is well-suited for separating the proteins from the extract based on their sugar-binding specificity. Other separation procedures may be utilized provided that an accurate measurement of each of the selected sugar-binding proteins is provided.

The five $Ca^{++}$ dependent and non-$Ca^{++}$ dependent sugar-binding proteins which are measured in accordance with the present invention are those that bind with lactose, galactose, melibiose, N-acetyl-D-galactosamine or fucose. The relative weight percentage of each of the sugar binding proteins (both $Ca^{++}$ dependent and non-$Ca^{++}$ dependent) which are necessary for an extract to meet the requirements of this preferred extract of the present invention are set forth in Table 1.

TABLE 1

COMPOSITION REQUIREMENTS FOR PHARMACEUTICAL GRADE KOREAN MISTLETOE EXTRACT

|  | Percentage By Weight of Total Protein in Extract |
|---|---|
| ($Ca^{++}$ dependent sugar-binding proteins) | |
| 1. Lactose | 0.1–0.5 |
| 2. Galactose | 0.1–0.5 |
| 3. Melibiose | 0.1–0.5 |
| 4. N-Acetyl-D-galactosamine | 0.1–0.5 |
| 5. Fucose | 0.1–0.5 |
| (Non-$Ca^{++}$ dependent sugar-binding proteins) | |
| 1. Lactose | 0.1–0.5 |
| 2. Galactose | 0.1–0.8 |
| 3. Melibiose | 0.1–0.5 |
| 4. N-Acetyl-D-galactosamine | 0.1–0.7 |
| 5. Fucose | 0.1–0.5 |

The relative percentage of each sugar-binding protein with respect to the total protein content of the extract will remain fairly constant irrespective of extraction conditions. However, the actual concentration levels of the various sugar-binding proteins will vary in each extract depending upon a number of factors including the relative amounts of mistletoe and aqueous extractant, the length of extraction and temperature. It is preferred that the extract be analyzed to determine the concentration levels of the various specified sugar-binding proteins and that these concentration levels be used to determine whether an extract meets the requirements for the mistletoe extract of the present invention. However, the extract may be diluted or concentrated to achieve protein concentration levels outside the preferred concentration ranges provided that the relative percentages of the sugar-binding proteins with respect to total protein levels remain within the limits set forth in Table 1. The extract, once it has been identified as meeting the requirement set forth in Table 1, may be dehydrated, and stored as a powder for rehydration and use at a later time to treat AIDS or cancer. An extract which meets the requirements of the present invention is considered to be a pharmaceutical grade mistletoe extract. The term "pharmaceutical grade" when used in this specification means that certain specified pharmacologically active ingredients in the mistletoe extract are within the absolute and/or relative concentration limits set forth in this specification and that the ingredients exhibit the activity levels set forth in this specification. The pharmaceutical grade mistletoe extracts of the present invention are particularly well-suited for use in clinical studies and treatment of patients in general.

The preferred concentration of all ten sugar-binding protein fractions (lectins) in a preferred extract are set forth in Table 2. In a further preferred embodiment, the bioactivity of the above isolated various lectins may be used in combination with their respective concentration levels to further identify the extract as meeting the requirements of the present invention. The various proteins which make up each of the $Ca^{++}$ dependent sugar-binding protein groups must each exhibit an inhibitory concentration of between about 0.01 and 0.5 μg/ml. The proteins which make up each of the non-$Ca^{++}$ dependent sugar-binding groups must also each exhibit an inhibitory concentration of between about 0.0001 and 0.1 μg/ml.

The method for measuring inhibitory action is set forth in numerous scientific articles including the references mention previously. It is preferred that the inhibitory action be measured in vitro with respect to leukemia L1210 cells. This procedure is preferred because L1210 cells are readily available, they are easily maintained by well-known culturing procedures and provide consistently reproducible results. The inhibitory concentration of each sugar-binding protein fraction is determined by adding increasing amounts of the fraction and determining when cell growth is inhibited by 50% as compared to a control culture. It is preferred that both the concentration level and the inhibition concentration of each of the sugar-binding proteins be measured and that they all be within the ranges set forth above and in Table 2.

TABLE 2

COMPOSITION REQUIREMENTS FOR PHARMA-
CEUTICAL GRADE KOREAN MISTLETOE EXTRACT

|  | Concentration (mg/ml) | Inhibitory Activity ($ID_{50}$) |
|---|---|---|
| ($Ca^{++}$ dependent sugar-binding proteins) | | |
| 1. Lactose | 0.1–0.5 | 0.1–0.5 |
| 2. Galactose | 0.2–0.6 | 0.1–0.5 |
| 3. Melibiose | 0.1–0.5 | 0.1–0.5 |
| 4. N-Acetyl-D-galactosamine | 0.5–1.0 | 0.1–0.5 |
| 5. Fucose | 0.1–0.5 | 0.1–0.5 |
| (Non-$Ca^{++}$ dependent sugar-binding proteins) | | |
| 1. Lactose | 0.1–0.5 | 0.0001–0.009 |
| 2. Galactose | 1.0–2.0 | 0.001–0.01 |
| 3. Melibiose | 0.1–0.5 | 0.001–0.01 |
| 4. N-Acetyl-D-galactosamine | 0.5–1.0 | 0.001–0.1 |
| 5. Fucose | 1.0–2.0 | 0.001–0.1 |

Once the concentration levels and/or inhibitory concentration of the designated sugar-binding proteins has been established, the extract is identified as meeting the compositional requirements of the present invention and therefor being of pharmaceutical grade. If one or more requirements are not met, the extract is rejected. The extracts which are identified as meeting the composition requirements are then used in treatment programs for treating diseases such as AIDS and cancer. The extracts are not only useful in treating AIDS, but they may be used to treat any individual with a suppressed immune system. If the extract has protein levels which are above the limits set forth above, the extract may be diluted as required to bring the extract protein concentrations down to the established limits. If the extract protein levels are below the limits, the extract is rejected.

It is preferred that the extract be initially screened for overall activity before beginning the more rigorous analysis of the sugar-binding protein fingerprint. It was discovered that extracts which do not meet certain total activity levels will also not meet the more specific protein fingerprint requirements of the present invention. The activity units are determined in the same manner as for the individual protein fraction with the only difference being that the entire extract is being tested. In accordance with the present invention, the extract must have and activity of greater than 100 A.U. Table 3 sets forth the results of initial screening wherein a number of different mistletoe extracts were screened to determine their biological activity using the L1210 cells as previously described. As can be seen, commercial preparations, such as ISCADOR, do not meet the initial screening test. The ISCADOR extracts also do not meet the more stringent specific protein fingerprint requirements of the present method. However, the extract n-T4GEN, which does meet the specific protein concentration fingerprint of the present invention, has activity levels well above the minimum of 100 A.U. The screening procedure is preferred because it allows non-suitable extracts to be identified relatively quickly without having to conduct the more time consuming protein fingerprinting. Once the Korean mistletoe extract passes this initial screening step, it then still must meet the further protein fingerprint requirements in order to meet the composition requirements of the present invention.

TABLE 3

BIOLOGICAL ACTIVITY OF MISTLETOE EXTRACTS
IN TERMS OF ACTIVITY UNITS (A.U.)

| Sample Identity | Activity units/ml, (1% Extract) |
|---|---|
| 1. ISCADOR M, Arg., 10% | 80 |
| 2. n-T4GEN, 40% | 400 |
| 3. ISCADOR M, 5% | 30 |
| 4. ISCADOR M, 20% | 37 |
| 5. T4GEN, 1% | 140 |
| 6. T4GEN, 10% | 217 |
| 7. ISCADOR M, 20% | 26 |
| 8. n-T4GEN, 40% | 416 |
| 9. n-T4GEN | 192 |
| 10. n-T4GEN | 811 |

$$\text{Activity unit per ml} = \frac{\text{concentration of sample in μg/ml}}{ID_{50} \text{ (μg/ml)}}$$

In use, the extracts may be used as is or diluted with suitable pharmaceutical carriers and administered according to known procedures for treating AIDS or a particular cancer. For treating AIDS, the extract is preferably injected subcutaneously in doses corresponding to from 0.01 ml to 1 ml of 1 percent extract and adjusted in relation to A.U. The injections are preferably given twice a week, but may be given more often. For cancerous tumors, the extract is injected directly into the tumor or may be injected subcutaneously.

The Korean mistletoe extract identified herein as n-T4GEN was tested to demonstrate its anti-HIV activity. N-T4GEN was analyzed and found to meet the sugar-binding protein fingerprint set forth in Table 2. The amount of protein in the alkaloidal and viscotoxin fractions were also found to be within the required fingerprint ranges. N-T4GEN was added to culture wells in an amount sufficient to provide concentration of 1 μl of 1 percent extract per ml of test solution (10 μg). This concentration of n-T4GEN inhibited HIV-induced cytopathic effects in H9 lymphoid human leukemia cells with concomitant reduction in viral reverse transcriptase levels in the infected cells.

Human immunodeficiency virus (HIV) infects T4 lymphocytes. In the H9 human lymphoma cell line, the virus produces giant multinucleated syncytial cells. After 3–6 days of viral infection the number of syncytia correlates with the degree of virus growth as quantified in the presence and absence of the drug being tested. These cytopathetic effects and assay of viral reverse transcriptase were used to demonstrate anti-HIV effects of n-T4GEN.

The anti-HIV assay using 1 μl/ml of a 1 percent n-T4GEN extract per ml of test solution was conducted as follows:

HIV inoculum was standardized for reverse transcriptase (RT) activity using purified avian myeloblastosis viral RT (BRL Labs, Gaithersberg, Md.) and used to infect polybrene treated H9 cells at 0.02 RT units of HIV per $2\times10^6$ cells. The virus was adsorbed for 2 hours at 37° C. and then the cells were washed twice and resuspended in RPMI 1640 containing 10% fetal bovine serum at $2\times10^5$ cells/ml and dispersed in 1 ml aliquots into 24-well plates (Falcon Division, Beckton Dickinson Co., Cockneyville, Md.). Syncytial giant cell formation appeared at 5–6 days post infection, and this cytopathic effect (CPE) was quantitatively measured by dispersing 0.1 ml aliquots into 0.1 ml absolute methanol and enumerating the giant cells microscopically. The inhibition of CPE by antiviral treatment with 1 μl of 1 percent extract was compared to untreated, infected H9 cells.

Reverse transcriptase activity was measured using 1 ml culture aliquots which were clarified at 600 xg for 30 minutes, precipitated in 10% polyethylene glycol—0.13M NaCl at 4° C. for 18 hours, and centrifuged at 600 xg for 60 minutes. The pellet was dissolved in glycerol-Tris buffer (50% glycerol, 25 mM Tris HCl pH 7.5, 5 mM dithiothreitol, 15 mM KCl, 0.025% Triton-X, and 0.25 mM EDTA). The RT assay was adapted from the methods of J. Levy et at., Science 225, 840 (1984); D. D. Ho et at., ibid 226, 451 (1984) using a final reaction mixture containing 40 mM Tris-HCl pH 7.8, 2.2 mM dithiothreitol, 10 mM $MgCl_2$, 50 mM KCl, 0.03% Triton-X, 25 μCi $^3$H-thymidine triphosphate (New England Nuclear, Boston, Mass.), and 50 μg/ml poly rA oligo $^{dT}$12–18 (BRL, Gaithersburg, Md.). Background counts were determined using poly dA oligo dT 12–18 as template and subtracted from the poly rA dT primer cpm to determine the thymidine incorporation specifically due to RT-activity.

The results of the tests are set forth as follows:

| Effect of Korean Mistletoe Extract on the Infectivity of HIV to H9 Lymphoma Cells in Culture | | |
|---|---|---|
| n-T4GEN* (μg/ml) | Cytopathic Effects (Syncytia cells) Day 5 | Reverse Transcriptase (cpm) Day 10 |
| 0.01 | ++ | 97,896 (100) |
| 0.10 | ++ | 77,971 (79) |
| 1.00 | ++ | 65,932 (67.3) |
| 10.00 | ± | 32,128 (32.8) |
| 100.00 | (toxic) | 4,200 |

H9 lymphoma cells growing in RPMI-1640 media containing 10% fetal calf serum were infected with HIV (100,000 RT counts) on day 1 and various concentrations of n-T4GEN extract. On day 5 cells were observed for cytopathic effects (syncytia), and on day 10 assayed for RT activity. (++) Denotes extensive giant cells, (±) fewer syncytial cell.
*Amounts expressed as μg/ml of 1 percent extract.

The results show that n-T4GEN at non-toxic concentrations inhibited HIV-induced cytopathic effects on H9 lymphoma cells. At these concentrations (10 μg/ml) there was also a significant (67.2%) inhibition of the viral reverse transcriptase.

Anticancer activities of n-T4GEN were studied in animals bearing subcutaneous transplants of C3H Mammary adenocarcinoma 16/C. This tumor is maintained as a lung passed tumor in C3H female mice. In this example, tumors ($1\times10^6$ cells) were transplanted (S.C.) in 18–20 g $B6C3F^1$ hybrid female mice. On the following day, the tumor bearing animals were randomized and separated into different treatment groups (10 mice per group). There were 15 animals in the control group who received only physiological saline during the treatment periods. The treatments (i.p.) were started 48 hours after the transplants and given for a duration of 14 days (daily single injections). Animals were weighed on days 5, 9 and 14 to assess toxic effects. Tumors were measured on days 21, 28 post transplants and the results are represented as tumor weights using formula $$\frac{1 \times w^2}{2}$$

($l$ = length of tumor, $w$ = width of tumor expressed in mm).

The results set forth below show that the n-T4GEN (5 mg/kg, qd 1–14) caused 33% inhibition growth of mammary adenocarcinoma 16/C, however, 30% of the treated animals remained tumor free until the termination of the experiment (day 93). This animal model is an accepted model for human breast carcinomas. The results were as follows:

| Effect of n-T4GEN on the Growth of Subcutaneous Transplants of C3H Mammary Adenocarcinoma 16/C in B6C3F1, Female Mice | | | | |
|---|---|---|---|---|
| Treatments i.p. | Δ Wts (g) (day 14) | Tumor Wts (day 21) | Tumor Inhibition % | Tumor Free Animals (day 93) |
| 1. Saline, Controls | +0.21 | 0.27 | — | 1/15 |
| 2. n-T4GEN* | | | | |
| 0.25 ml/kg, qd (1–14) | +1.33 | 0.15 | 44 | 1/10 |
| 0.5 ml/kg, qd (1–14) | +0.73 | 0.18 | 33 | 3/10 |
| 3. 5Fluorouracil | | | | |
| 98 mg/kg, qd (1,7,14,21) | +1.77 | 0.00 | 100 | 0/6 |

*Amounts expressed as ml of 1 percent extract.

Examples of practice of the invention are as follows:

EXAMPLE 1

Preparation of Pharmaceutical Grade Mistletoe Extract from Korean Mistletoe (n-T4GEN)

Plant powder (2.4 Kg) obtained from Korean mistletoe was extracted with 300 ml batches of water in a clean blender. The extract was filtered through cheese cloth lined filter beds to eliminate fibrous and water-insoluble residues, final volume 6.03 liters. Final concentration of the extract was 39.8% (plant weight/volume).

The extract was left at 4° C. for two weeks in absence of air (flushed with nitrogen). At this time additional insoluble residues were deposited. The cold extract was filtered through 0.8μ filters and final sterile filtration was performed with 0.2 micron filters and in sterile environment. The semi-purified product was collected in 500 ml sterile vacuum containers and identified as n-T4GEN. The product samples were found to be pyrogen free. Samples from the flask were removed with a sterile syringe in a laminar flow hood and diluted on the basis that each ml of the sample contains 400 mg of the extract, i.e. a 40 percent extract.

The extract samples were analyzed according to the affinity chromatography system schematically shown in the FIGURE. The columns used to separate the proteins were Sepharose® 4B.

The columns were prepared as follows:

Activation of Sepharose 4B: Sepharose 4B (400 ml) was repeatedly washed with double distilled water and filtered on a buchner funnel. The sepharose residue was repeatedly washed with $Na_2CO_3$ (0.5M, pH 11) and then suspended in a stirred 2 liter cylinder in 400 ml $Na_2CO_3$ (0.5M, pH 11). The cylinder was covered with aluminum foil and to the stirred suspension of Sepharose 4B, divinylsulfone (48 ml, absence of light) was added dropwise over a period of 80 minutes. The reactants were stirred for another 30 minutes at room temperature. Then the resin was filtered on a sintered glass funnel (no touching with hands or paper) with approximately 500 ml of $Na_2CO_3$ (0.5M, pH 10, make with $NaHCO_3$). At this time the resin was suspended in 400 ml $Na_2CO_3$ (0.5M, pH 10) and used for preparing sugar-specific affinity resins as follows:

Galactose-specific Sepharose 4B: To the activated resin 380 ml (in 5M $Na_2CO_3$), galactose (38 g) was added with stirring in absence of light. The suspension was stirred overnight and then the suspension was filtered on a sintered glass funnel. To inactivate the reacted activated sepharose, the residue was washed with 0.5M $NaHCO_3$ (pH 8.5) and then suspended in 350 ml $NaHCO_3$ (0.5M, pH 8.5) and 14 ml 2-mercaptoethanol. The stirred suspension was maintained at room temperature for 4 hours and then filtered on a sintered glass funnel. The resin was washed with 0.2M PBS (phosphate buffered saline) and finally suspended in 380 ml 0.2M PBS and stored at 4° C. along with a few crystals of $NaN_3$.

Lactose-specific Sepharose 4B: The method of preparation was the same as described for galactose. Here 300 ml of activated Sepharose was reacted with 30 g of lactose and the affinity resin was deactivated with 300 ml $NaHCO_3$ (0.5M, pH 8.5), 12 ml 2-mercaptoethanol and finally suspended in 300 ml of PBS and $NaN_3$ as described in the previous preparation.

N-Acetyl-D-galactosamine-specific Sepharose B: Activated Sepharose 4B (30 ml) was treated with 3 g of N-acetyl-D-galactosamine as described. The reaction was terminated with 30 ml $NaHCO_3$ (0.5M, pH 8.5) and 5 ml 2-mercaptoethanol. The resin was maintained in 30 ml PBS and a few crystals $NaN_3$ at 4° C.

Fucose-specific-Sepharose 4B: Activated Sepharose (50 ml) was reacted with 5 g fucose. The affinity resin was treated with 50 ml $NaHCO_3$ and 5 ml 2-mercaptoethanol to deactivate the unreacted Sepharose. The resin was maintained in 50 ml PBS and $NaN_3$ as described.

Melibiose-Specific Sepharose 4B: Activated Sepharose 4B (50 ml) was created with 5 g melibiose. The reaction was terminated with 50 ml $NaHCO_3$ and 5 ml mercaptoethanol. The resin was maintained in 50 ml PBS and a few crystals of $NaN_3$ at 4° C.

The same methods can be used to provide columns of different sugar specificity. The used columns were regenerated by elutions with 5M urea and followed by elution with 0.5M $NaHCO_3$ (pH 8.5). Prior to use, columns are equilibrated with 0.02M Tris/HCl buffer (Buffer C).

The Buffers used for Extraction and Affinity Chromatography were prepared as follows:

All buffers made in double distilled water (DD).

A) Tris/HCl (0.02M, pH 7.8) containing NaCl (0.2M) dithiothreitol (1 mM) and just use add phenyl methanesulfonyl fluoride (0.01 mM). (Buffer A).

B) Tris/HCl (0.02M, pH 7.8) containing 0.4M KCl, 2% Triton x-100, 1 mM dithiothreitol and 0.01 mM phenyl methanesulfonyl fluoride (to be added before use). (Buffer B).

C) Tris/HCl (0.02M, pH 7.8) containing 1.25M NaCl, 25 mM $CaCl_2$, 0.05% Triton x-100 and 1 mM dithiothreitol. (Buffer C).

D) Buffer (C) containing 4 mM EDTA instead of 25 mM $CaCl_2$. (Buffer D).

A known volume of the mistletoe extract was adjusted to pH 7.8 with 2M tris-buffer. The solution was absorbed on a series of Sepharose® 4B affinity columns (1.6×7 ml). The columns were washed with excess of (200 ml) of 0.02M tris-buffer (pH 7.8) containing 25 mM $CaCl_2$ (Buffer C) to remove all unbound proteins (viscotoxins and alkaloids). Then each column was separately washed with tris-buffer (pH 7.8) containing 4 mM EDTA (Buffer D) to elute proteins which require $Ca^{++}$ for their binding to specific sugars i.e. $Ca^{++}$ dependent sugar-binding proteins (100 ml samples). Subsequently, the columns were washed with tris-buffer (Buffer C, 200 ml) and then eluted with the same buffer (100 ml) containing 0.5M corresponding sugars to remove non-$Ca^{++}$ dependent sugar binding proteins. The unbound proteins were fractionated on a Sephadex G-75 column (2.5×75 cm) to separate viscotoxins from alkaloids. All fractions were dialyzed to remove salts and other buffer ingredients. Each dialyzed fraction was concentrated by Amicon concentrator using DIAFLO ultrafiltration membrane YM10 (10,000 cutoff). Protein concentration was measured by Bio-rad assay with bovine-globulin as a standard (each separated protein may be characterized for its purity and molecular weight by SDS page gel chromatography).

The inhibitory concentration ($ID_{50}$) was determined for each sugar-binding protein as follows:

Leukemia L1210 was maintained in asynchronous logarithmic growth at 37° C. in RPMI 1640 medium supplemented with 10% (v/v) fetal bovine calf serum and 1% (v/v) Pen Strep. The cell population doubling time was 11–12 hours. The cells were passed every 48 hours at $1\times10^4$ cell/ml in order to keep the cells in logarithmic stage of growth.

For all growth inhibition studies all stock solutions and dilutions were made with sterile 0.7% NaCl solution. The cell cultures were seeded at $2-5\times10^4$ cells/ml in duplicates for each inhibitor concentration in a microtiter plate (0.18 ml/well). The covered microtiter plate was incubated for 48 hours in a humidified $CO_2$ incubator containing 5% $CO_2$ in air. At the end of the incubation period, aliquots of each well were added to a measured volume of isotonic saline and counted in an electronic counter. Because fractions at high concentrations caused rapid cellular fragmentation, the test microtiter plates were routinely checked under a microscope prior to cell number counting so that the results were not compromised. The cell viability was determined by trypan blue exclusion. The results were calculated by plotting percent cell growth inhibition (as compared to the cell density of the saline treated controls) versus log of protein (or specific fraction) concentration which caused 50% inhibition ($ID_{50}$) in cell growth as determined from the graph.

The results of the analysis are shown in Tables 4 and 5 for n-T4GEN salt and detergent extracts prepared in accordance with this example. As can be seen from Tables 4 and 5, the extracts from both the sap and the cell walls of the Korean mistletoe have protein levels and inhibitory activities which all fall with the limits required to meet the requirements of a pharmaceutical grade protein extract in accordance with the present invention. Accordingly, this extract, after removal of salts and detergents, may be used in clinical studies directed to cancer or AIDS treatment. It may also be used for routine patient treatment since its quality and efficacy has been established in accordance with the preferred protein fingerprint identifiers required in accordance with the present invention.

TABLE 4

**FRACTIONATION OF THE VARIOUS CONSTITUENTS OF *V. ALBUM* COLORATUM WITH ANTILEUKEMIA — L1210 ACTIVITY — n-T4GEN (40%)**
(Affinity Method, Fractionation of Salt Extract)

| Fraction identity | Protein Content (mg/ml) | Total Volume (ml) | Total Protein (mg) | $ID^a_{50}$ (µg Protein/ml) | Total Activity[b] Units |
|---|---|---|---|---|---|
| Salt Extract | 7.63 | 350 | 2673 | 0.11 | $2.4 \times 10^7$ |
| Affinity columns eluted with EDTA buffer — $Ca^{++}$ dependent | | | | | |
| 1. Lactose | 0.31 | 20 | 6.24 | 0.38 | $1.6 \times 10^4$ |
| 2. Galactose | 0.39 | 20 | 7.91 | 0.25 | $3.1 \times 10^4$ |
| 3. Melibiose | 0.28 | 20 | 5.44 | 0.20 | $2.7 \times 10^4$ |
| 4. N-Acetyl-D-galactosamine | 0.70 | 12.5 | 875 | 0.29 | $3.00 \times 10^4$ |
| 5. Fucose | 0.28 | 18 | 5.04 | 0.36 | $1.4 \times 10^4$ |
| Affinity columns eluted with corresponding sugars — non-$Ca^{++}$ dependent | | | | | |
| 1. Lactose | 0.27 | 22 | 5.98 | 0.00027 | $2.2 \times 10^7$ |
| 2. Galactose | 1.40 | 9 | 12.60 | 0.0013 | $9.6 \times 10^6$ |
| 3. Melibiose | 0.32 | 10 | 3.20 | 0.0034 | $9.4 \times 10^5$ |
| 4. N-Acetyl-D-galactosamine | 0.66 | 18 | 11.90 | 0.017 | $7.0 \times 10^5$ |
| 5. Fucose | 1.17 | 15 | 2.59 | 0.019 | $1.3 \times 10^5$ |
| Sephadex — G75 (Unbound proteins) Fractions[c] | | | | | |
| I (12–50) | 1.84 | 46 | 84.6 | 0.5 | $1.69 \times 10^5$ |
| II (51–70) | 1.22 | 22.5 | 27.45 | 4.0 | $6.8 \times 10^3$ |
| III (71–100) | 1.12 | 40 | 44.80 | 2.8 | $1.6 \times 10^4$ |
| IV (101–140)[d] | -0- | 50 | -0- | 13.5 | $1.6 \times 10^4$ |

[a]Inhibitory concentration expressed as µg protein/ml which caused 50% inhibition of the growth of L1210 cells in culture.
[b]Activity unit is defined as dilution factor needed for a specific fraction which when added to L1210 cells caused a 50% cell growth inhibition.
[c]50 ml on column from a total eluate of 325 ml.
[d]31 mg alkaloids obtained from fraction IV.

TABLE 5

**FRACTIONATION OF THE VARIOUS CONSTITUENTS OF *V. ALBUM* COLORATUM WITH ANTILEUKEMIA — L1210 ACTIVITY — n-T4GEN (40%)**
(Affinity Method, Fractionation of Detergent Extract)

| Fraction Identity | Protein Content (mg/ml) | Total Volume (ml) | Total Protein (mg) | $ID^a_{50}$ (µg Protein/ml) | Total Activity[b] Units |
|---|---|---|---|---|---|
| Detergent Extract | 1.68 | 450 | 756 | 0.27 | $2.8 \times 10^6$ |
| Affinity columns eluted with EDTA buffer | | | | | |
| 1. Lactose | 0.18 | 22 | 4.04 | 0.250 | $1.6 \times 10^4$ |
| 2. Galactose | 0.08 | 11.5 | 0.97 | 0.031 | $3.1 \times 10^4$ |
| 3. Melibiose | 0.16 | 20 | 3.12 | 0.054 | $5.7 \times 10^4$ |
| 4. N-Acetyl-D-galactosamine | 0.17 | 19 | 3.20 | 0.076 | $4.2 \times 10^4$ |
| 5. Fucose | 0.12 | 6.5 | 0.78 | 0.100 | $0.5 \times 10^4$ |
| Affinity columns eluted with corresponding sugars | | | | | |
| 1. Lactose | 0.35 | 95 | 3.23 | 0.0045 | $2.1 \times 10^6$ |
| 2. Galactose | 0.50 | 15 | 7.50 | 0.0055 | $1.3 \times 10^6$ |
| 3. Melibiose | 0.15 | 12 | 0.61 | 0.0084 | $0.07 \times 10^6$ |
| 4. N-Acetyl-D-galactosamine | 0.62 | 4 | 7.68 | 0.0035 | $2.1 \times 10^6$ |
| 5. Fucose | 0.50 | 10 | 5.10 | 0.0500 | $0.1 \times 10^6$ |
| Sephadex — G75 (Unbound proteins) Fractions[c] | | | | | |
| I (9–35) | 1.58 | 33 | 52.1 | 1.25 | $0.05 \times 10^6$ |
| II (36–55) | 1.36 | 20 | 27.2 | 1.70 | $0.008 \times 10^6$ |
| III (56–120)[d] | -0- | 50 | -0- | 14.00 | $0.002 \times 10^6$ |

[a]Inhibitory concentration expressed as µg protein/ml which caused 50% inhibition in the growth of L1210 cells in culture.
[b]Activity unit is defined as dilution factor needed for a specific fraction which when added to L1210 cells caused a 50% inhibition.
[c]50 ml on column from a total of 420 ml.
[d]22 mg alkaloids obtained from fraction III.

The protein contains fractions (12–100) with biological activity in L1210 system obtained from Sephadex G75 column (see Table 1) contained a mixture of viscotoxins (1.019 g). The fractions (101–140) were combined and extracted with 3×200 ml) chloroform. The chloroform layer was dried over anhydrous $Na_2SO_4$, filtered and the filtrate was evaporated under vacuum to obtain 201 mg of alkaloids as confirmed by Dragendorff test (weights of viscotoxins and alkaloids set forth in Table 1 are adjusted to a total of 325 ml for the unbound fraction obtained from affinity columns). The 40% extract has lectins, viscotoxins and A.U. or more. If the extract passes this test, then it is subjected to the more rigorous tests as described in Example 1 to determine its sugar-binding protein fingerprint. If the protein levels fall within the limits required in accordance with the present invention, then the extract is identified as pharmaceutical grade. Table 6 sets forth the results of testing of an extract prepared as above. As can be seen, the extract has concentration levels and percentages which fall within the limits required for it to be a mistletoe extract in accordance with the present invention.

TABLE 6

FRACTIONATION OF DIFFERENT BIOLOGICALLY ACTIVE CARBOHYDRATE BINDING PROTEINS FROM *VISCUM ALBUM* C. EXTRACT (40%, FrF) (n-T4GEN)

| Fraction identity | Total Volume (ml) | Total Protein (mg) | $ID_{50}{}^a$ | $ID_{50}{}^a$ (μg/ml) | Total Activity Units[b] |
|---|---|---|---|---|---|
| Extract (40%, FrF) | 90 | 234 | 32,500 | | $2.92 \times 10^6$ |
| Affinity columns eluted with EDTA buffer | | | | | |
| 1. Lactose | 5.5 | 4.29 | 175 | 1.10 | $0.10 \times 10^4$ |
| 2. Galactose | 11.5 | 2.10 | 415 | 0.49 | $0.50 \times 10^4$ |
| 3. Melibiose | 10 | 1.36 | 315 | 0.40 | $0.30 \times 10^4$ |
| 4. N-Acetyl-D-galactosamine | 7 | 0.95 | 400 | 0.33 | $0.28 \times 10^4$ |
| 5. Fucose | 5 | 1.82 | 365 | 1.00 | $0.18 \times 10^4$ |
| Affinity columns eluted with buffer containing corresponding sugars | | | | | |
| 1. Lactose | 8 | 2.24 | 208,000 | 0.001 | $1.66 \times 10^6$ |
| 2. Galactose | 11 | 2.68 | 68,000 | 0.0035 | $0.75 \times 10^6$ |
| 3. Melibiose | 6.5 | 0.96 | 5,600 | 0.025 | $0.036 \times 10^6$ |
| 4. N-Acetyl-D-galactosamine | 4.5 | 0.81 | 49,000 | 0.0035 | $0.22 \times 10^6$ |
| 5. Fucose | 5 | 0.33 | 10,500 | 0.0056 | $0.052 \times 10^6$ |
| Unbound proteins and alkaloids | 168 | 285 | 1,600 | 1.25 | $0.27 \times 10^6$ |

[a]Dilution factor needed per ml to cause 50% inhibition of L1210 cells in culture.
[b]Activity unit is defined as dilution factor needed for a specific fraction which when added to L1210 cell will cause 50% inhibition of the cell growth.

alkaloid levels which are equivalent to a 1 percent extract which contains 4.9 μg lectins, 72 μg unbound protein which contains 10–40 μg viscotoxins and 14.3 μg alkaloids which meets the requirements of the present invention.

EXAMPLE 2

Preparation of Double Distilled Water Extract

An extract from Korean mistletoe was prepared by taking a known weight of plant (100 g) and cleaning and crushing it in the presence of double distilled water to form a 40% by weight solution of mistletoe. It is preferred that the plant be cut and the cuttings put in a plastic bag and flash frozen in liquid nitrogen prior to being crushed and combined with the distilled water. The crushing and combination of the frozen material with the distilled water is preferably carded out in a blender for about 2 minutes. The resulting mixture is centrifuged at 10,000 rpm for 65 minutes to separate extract from insoluble residue. The residue is twice extracted with known volumes (100 ml) of water to remove all extract and subjected to centrifugation. The supernatants are combined. The resulting extract is stored in the absence of air at room temperature for two weeks. The extract is then sterilized by step filtration as is conventionally known.

The sterile extract is then subjected to a preliminary screening test as previously described to determine if its bioactivity with respect to the L1210 leukemia system is 100

EXAMPLE 3

Preparation of Total Extract of Korean Mistletoe

An extract of Korean mistletoe was prepared by taking 100 g of mistletoe, freezing it and powdering it. The frozen powder was then thawed and extracted with 200 ml of cold acetone. The extraction mixture was centrifuged at 10,000 rpm for 60 minutes. The precipitate was washed with two 100 ml aliquots of cold acetone and centrifuged again at 10,000 rpm for 60 minutes. The resulting extract residue is extracted with two 200 ml aliquots of Buffer A (see Example 1) in a blender for 2 minutes each. The two extract aliquots are centrifuged at 10,000 rpm for 60 minutes and the supernatants combined. The extract residue is extracted a final time with an additional 200 ml of Buffer A. After centrifugation, this final extractant is combined with the other two aliquots to form a salt extract which is then tested in accordance with the preferred embodiment of the present invention to determine if its lectin, alkaloidal fraction and viscotoxin levels, as well as its sugar-binding protein fingerprint, meets the compositional requirements set forth above.

The scientific articles and other references referred to in this specification are hereby specifically all incorporated by reference.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. An extract of Korean mistletoe which comprises lectins, viscotoxins, alkaloids and one or more $Ca^{++}$ dependent sugar-binding proteins, said sugar-binding proteins being selected from the group consisting of proteins in said extract which bind to lactose, galactose, melibiose, N-acetyl-D-galactosamine and fucose, wherein the concentrations of said lectins, viscotoxins, alkaloids and $Ca^{++}$ dependent sugar-binding proteins corresponds to:

8.0 to 12 µlectins, 10 to 30 µg viscotoxins, 1 to 40 µg alkaloids and 0.1 to 1.0 mg sugar-binding protein per milliliter of extract wherein said extract is prepared by extracting Korean mistletoe in amounts equivalent to 1 gram of mistletoe per 100 milliliters of extractant.

2. An extract of Korean mistletoe according to claim 1 wherein the inhibitory concentration of said one or more sugar-binding proteins is between 0.1 and 0.50 µg/ml.

3. The extract of Korean mistletoe according to claim 1 wherein said extract comprises one or more non-$Ca^{++}$ dependent sugar-binding proteins, said non-$Ca^{++}$ dependent sugar-binding proteins being selected from the group of proteins in said extract which binds to lactose, galactose, melibiose, N-acetyl-D-galactosamine and fucose, wherein the concentrations of said non-$Ca^{++}$ dependent sugar-binding proteins corresponds to 0.1 to 2.0 mg/ml non-$Ca^{++}$ dependent sugar-binding protein per milliliter of said extract.

4. An extract of Korean mistletoe according to claim 3 wherein the inhibitory concentration of said one or more non-$Ca^{++}$ dependent sugar-binding proteins is between 0.0001 and 0.1 µg/ml.

5. An extract of Korean mistletoe according to claim 3 wherein the concentration of said $Ca^{++}$ dependent and/or non-$Ca^{++}$ dependent galactose binding proteins is between about 0.2 and 2.0 mg/ml and the inhibitory concentration of said galactose binding proteins is between about 0.001 and 0.5 µg/ml.

6. An extract of Korean mistletoe according to claim 5 wherein the concentration of said $Ca^{++}$ dependent and/or non-$Ca^{++}$ dependent melibiose binding proteins are between about 0.1 and 0.5 mg/ml and the inhibitory concentration of said melibiose binding proteins are between about 0.001 and 0.50 µg/ml.

7. An extract of Korean mistletoe according to claim 6 wherein the concentration of said $Ca^{++}$ dependent and/or non-$Ca^{++}$ dependent N-acetyl-D-galactosamine binding proteins are between about 0.1 and 1.0 mg/ml and the inhibitory concentration of said N-acetyl-D-galactosamine binding proteins are between 0.001 and 0.5 µg/ml.

8. An extract of Korean mistletoe according to claim 7 wherein the concentration of $Ca^{++}$ dependent and/or non-$Ca^{++}$ dependent fucose binding proteins are between about 0.1 and 2.0 mg/ml and the inhibitory concentration of said fucose binding proteins are between 0.001 and 0.5 µg/ml.

9. An extract of Korean mistletoe according to claim 5 wherein the concentration of said $Ca^{++}$ dependent and/or non-$Ca^{++}$ dependent lactose binding proteins are between about 0.1 and 0.5 mg/ml and the inhibitory concentration of said lactose binding proteins are between about 0.0001 and 0.5 µg/ml.

10. An extract of Korean mistletoe according to claim 1 wherein said extract comprises about 4.9 µg lectins, 10–40 µg viscotoxins and about 14 µg alkaloids per ml of extract.

11. A method for treating a mammal having AIDS with a mistletoe extract wherein said method comprises the step of administering to said mammal a therapeutically effective dose of a Korean mistletoe extract as set forth in claim 1.

12. A method for treating a mammal having cancer with a mistletoe extract wherein said method comprises the step of administering to said mammal a therapeutically effective dose of a Korean mistletoe extract as set forth in claim 1.

* * * * *